(12) United States Patent
Nakamura et al.

(10) Patent No.: US 6,508,585 B2
(45) Date of Patent: Jan. 21, 2003

(54) DIFFERENTIAL SCANNING CALORIMETER

(75) Inventors: Nobutaka Nakamura, Chiba (JP); Ryoichi Kinoshita, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/998,356

(22) Filed: Nov. 30, 2001

(65) Prior Publication Data

US 2002/0085615 A1 Jul. 4, 2002

(51) Int. Cl.[7] .......................... G01N 1/00; G01N 25/20; G01K 1/20; G01K 17/04; G01K 17/08
(52) U.S. Cl. .............. 374/12; 374/10; 374/11; 374/32
(58) Field of Search ................ 374/1, 32, 33, 374/11–13, 31, 43

(56) References Cited

U.S. PATENT DOCUMENTS

| 4,111,717 A | * | 9/1978 | Baxter | 73/355 R |
| 4,783,174 A | * | 11/1988 | Gmelin et al. | 374/33 |
| 4,812,051 A | * | 3/1989 | Paulik et al. | 374/10 |
| 5,288,147 A | * | 2/1994 | Schaefer et al. | 374/10 |
| 5,779,363 A | * | 7/1998 | Freire et al. | 374/33 |
| 5,842,688 A | * | 12/1998 | Danley et al. | 374/12 |
| 5,842,788 A | * | 12/1998 | Danley et al. | 374/12 |
| 5,967,659 A | * | 10/1999 | Plotnikov et al. | 374/11 |
| 6,079,873 A | * | 6/2000 | Cavicchi et al. | 374/10 |
| 6,390,669 B1 | * | 5/2002 | Nakamura et al. | 374/12 |

FOREIGN PATENT DOCUMENTS

JP 111602261 * 6/1999 .......... G01N/25/20

* cited by examiner

Primary Examiner—Diego Gutierrez
Assistant Examiner—Gail Verbitsky
(74) Attorney, Agent, or Firm—Adams & Wilks

(57) ABSTRACT

An insulating substrate provided with two types of metallic or alloy circuit patterns for detecting temperature difference between a sample side and a reference side, and also a metallic resistance circuit pattern, is fixed to a heat sink, and the heat sink is temperature controlled. If a temperature difference between the sample and the reference is detected, electrical power supplied to a compensation heater using metallic resistors is adjusted by a differential heat compensation circuit so that the temperature difference is immediately returned to zero, and a difference in supplied power is output as a differential heat flow.

4 Claims, 3 Drawing Sheets

DIFFERENTIAL SCANNING CALORIMETER

BACKGROUND OF THE INVENTION

1. Field of the Invention

The present invention relates to a thermal analyzer for measuring how the physical or chemical properties of a sample as a function of temperature, and particularly to a differential scanning calorimeter for measuring and analyzing a endothermic and exothermic phenomena of a sample by detecting a differential heat flow between sample and reference material under the condition of constant rate temperature change. Heat flow that a sample additionally generates or absorbs compared to a reference material when temperature is changed at a constant rate.

2. Description of the Related Art

A differential scanning calorimeter is a device for differentially detecting and analyzing heat flow that a sample additionally generates or absorbs compared to a reference material, when the temperature of both the sample and the reference material is changed at a constant rate with the sample and the reference material (alumina or the like is normally used for a thermally stable reference material) arranged symmetrically.

When the temperature of the sample rises at a constant rate, heat absorption by the sample increases as the heat capacity of the sample becomes large. Specifically, an absolute value of differential heat flow signal becomes large. At this time, from the fact that the absolute value of the differential heat flow signal is proportional to change in thermal capacity between the sample and a reference and to rate of temperature rise, the heat capacity of the sample can be known from original differential heat flow signal based on an already known rate of temperature rise and heat capacity of the reference.

On the other hand, when a sample is fused, heat absorption by the sample temporarily becomes large, and if the differential heat flow signal is recorded over time and plotted on a graph it will appear as an endothermic peak. Also, if the same recording method is used, then the differential heat flow signal will describe an exothermic peak if crystallization occurs in the sample. The surface area of these endothermic and exothermic peaks described on the time axis set up so that a unit time corresponds to a constant length is proportional to an amount of heat released or absorbed when the sample is in transition, which means that if an already known heat of transition is measured in advance and a signal value calibrated, it is possible to easily obtain the heat of transition of the sample from a differential heat flow signal. Differential thermal calorimeters are widely used in the analysis of various materials in order to obtain a differential heat flow signal having the above described useful characteristics.

Conventional differential scanning calorimeters are generally divided into the following two types.

First of all there are the power compensation type, comprising a combination of two independent calorimeters for a sample and for a reference arranged symmetrically, and respectively provided with a resistance temperature sensor and a heater for heat flux feedback. An average value of the temperatures detected by the two sensors is compared to a temperature output of a temperature program device varied at a constant rate, and the two calorimeters are heated by the heaters for heat flux feedback so that the average value and the temperature output coincide. Also, if there is a difference in temperature output of the two temperature sensors, electrical power of both heaters is immediately adjusted so that the difference returns to zero. At this time, a difference in electrical power supplied to the two heaters every second is recorded as a differential heat flux signal. A power compensation-type differential scanning calorimeter is extremely responsive, and is capable of realizing a thermal compensation time constant of less than two seconds.

There are also heat flux type calorimeters in which temperature sensors for a sample and a reference are fixed inside a heat sink formed of a superior heat conducting material so as to form symmetrical heat flow paths that are equal to each other. The temperature of the heat sink is compared to a temperature output of a temperature program device varied at a constant rate, and feedback control is performed using a heater wound around the heat sink so that the temperature of the heat sink and the output temperature coincide. A temperature difference between the sample and the reference is detected using a differential thermocouple. At this time, it is possible to obtain differential heat flux which is a difference between heat flow to the sample and heat flow to the reference, if the temperature difference between the sample and the reference is divided by the thermal resistance (reciprocal of thermal conductance) between the heat sink and the sample, this is similar to obtaining electrical current by dividing a potential difference by resistance, Specifically, with a heat flux type differential scanning calorimeter, an output of a differential thermocouple, representing a temperature difference between the sample and the reference, is appropriately amplified, and output and stored as a differential heat flow signal.

A heat flux type differential scanning calorimeter has excellent base line stability, but ordinarily has a thermal compensation time constant of over 3 seconds, which means there are problems such as the fact that a heat flow signal peak is not so sharp, and separation between a plurality of peaks becomes poor. With an power compensation type, it is possible to realize a thermal compensation time constant of less than two seconds but with respect to base line characteristics, it has been difficult to get stability as good as that of the heat flux type differential scanning calorimeter. The main reason for this is that there is a large temperature difference between the power compensation type sensor and the surrounding material during measurement, which means that there is constantly a comparatively large amount of heat leakage from the sensor to the outside, constituting the main cause of drift in the base line.

A method of combining a power compensation type detector and a heat sink formed of a material having a good heat conductivity, which is the main feature of the heat flux type calorimeter, has been disclosed, with the intention of solving the drawbacks of the above described two types of differential scanning calorimeter. In Japanese Patent Laid open No. Tokkaihei. 11-160261, there is disclosed a differential scanning calorimeter, comprising: a heat sink formed of a thermally good conductor and having a space for accommodating a sample at an inside;

a detector fixed within said heat sink and formed by an insulation substrate formed with symmetric circuit patterns of metal resistors;

a temperature measuring circuit for measuring a temperature of said detector by detecting resistance values of said metal resistors in said detector;

a differential temperature detecting circuit for comparing resistance values of one pair of metal resistance circuit to detect a temperature difference between a sample and a reference placed in said detector;

a program temperature function generator for outputting temperature target values in time;

a heat sink temperature controller for controlling a temperature of said heat sink depending on an output of said program temperature function generator;

a detector temperature controller for controlling a temperature of said detector by controlling current values flowing through said metal resistance circuits in said detector based on a comparison result of an output of said program temperature generator and output of said temperature measuring circuit;

a differential heat compensating circuit for causing a proper current to flow through each of said one pair of metal resistor in said detector such that an output of said differential temperature detecting circuit uninterruptedly returns to zero;

whereby low drift characteristic of a heat flux type and high responsibility of a power compensation type are both obtained.

As disclosed in Japanese Patent Laid-open No. Tokkaihei 11-160261, in a differential scanning calorimeter comprising a temperature detector having circuit patterns using metallic resistors and an insulating substrate having a compensation heater fixed inside a heat sink formed of a material having good heat conductivity, the temperature difference detecting circuit uses a bridge circuit, and detection is carried out by causing current to flow in the metallic resistors of the circuit patterns and detecting resistance values from potential differences of the bridge circuit. Accordingly, it is fundamentally impossible to avoid the fact that there is self-heat generation caused by the electrical current flowing in the metallic resistors themselves of the circuit pattern, being the temperature detector. As well as performing control of the compensation heater with the temperature difference sensor as a trigger, if there is temperature variation caused by self heat generation at the time of temperature detection with an initial trigger, this variation is amplified because of negative feedback of the compensation heater based on this temperature variation, and as a result there is a problem that it is difficult to obtain stable temperature control.

Also, in the differential temperature detecting circuit for detecting temperature difference, if the voltage applied to the bridge circuit is lowered in order to reduce self heat generation in the circuit pattern, a potential difference corresponding to the temperature difference is also reduced, and the electrical sensitivity of the temperature difference detection is lowered. On the other hand, it is necessary to raise the applied voltage in order to increase temperature difference detection sensitivity, and in this case there the dilemma that self heat generation in the circuit patterns increases.

SUMMARY OF THE INVENTION

In order to solve the above described problems, a differential scanning calorimeter according to the present invention has both a high response of power compensation type and a baseline stability of heat flux type and is provided with a heat sink made of a good heat conductive material and having a space for housing a sample and sample reference material inside; an insulating substrate fixed to the inside of the heat sink and setting a region for mounting the sample and the reference; first circuit pattern that has been applied so as to form junction of two kinds of alloy or metal at respective regions for mounting the sample and the reference on the insulating substrate; a differential temperature detector for detecting a thermal difference between the sample and the reference mounted on the insulating substrate by detecting a difference in thermoelectromotive force at junctions of sample side region and of the reference side region of the circuit pattern; second circuit patterns formed by means of metallic resistors respectively applied to regions for mounting the sample and the reference on the insulating substrate; a differential heat compensation circuit for allowing respectively appropriate currents of the second circuit patterns formed by means of metallic resistors on the insulating substrate to flow so as to continually return output of the differential thermal detection circuit to zero; a temperature program generator for outputting a target temperature value periodically; and a heat sink temperature controller for controlling temperature of the heat sink in response to output of the temperature program generator.

A sample and a reference are subject to temperature control utilizing thermal conduction from a heat sink controlled in response to a program temperature, through an insulation substrate. A temperature difference between the sample and the reference under temperature change is detected as a thermo electromotive force generated by a Seebeck effect of applied circuit patterns forming junction of two kinds of metal or alloy, and output to a differential heat compensation circuit. The differential heat compensation circuit adjusts the amount of electrical power to the respective metallic resistors applied to mounting regions for the sample and the reference so that a temperature difference immediately returns to zero, and metallic resistors act as heaters for power compensation provided individually close to the sample and the reference.

As a result, differences in absorbed or generated heat compared to the sample and the reference are detected as differences in power supplied to heaters provided individually close to the sample and the reference, and realize a function of a differential scanning calorimeter.

DETAILED DESCRIPTION OF THE INVENTION

The present invention will be described in detail in the following based on drawings showing embodiments.

Figure 1:
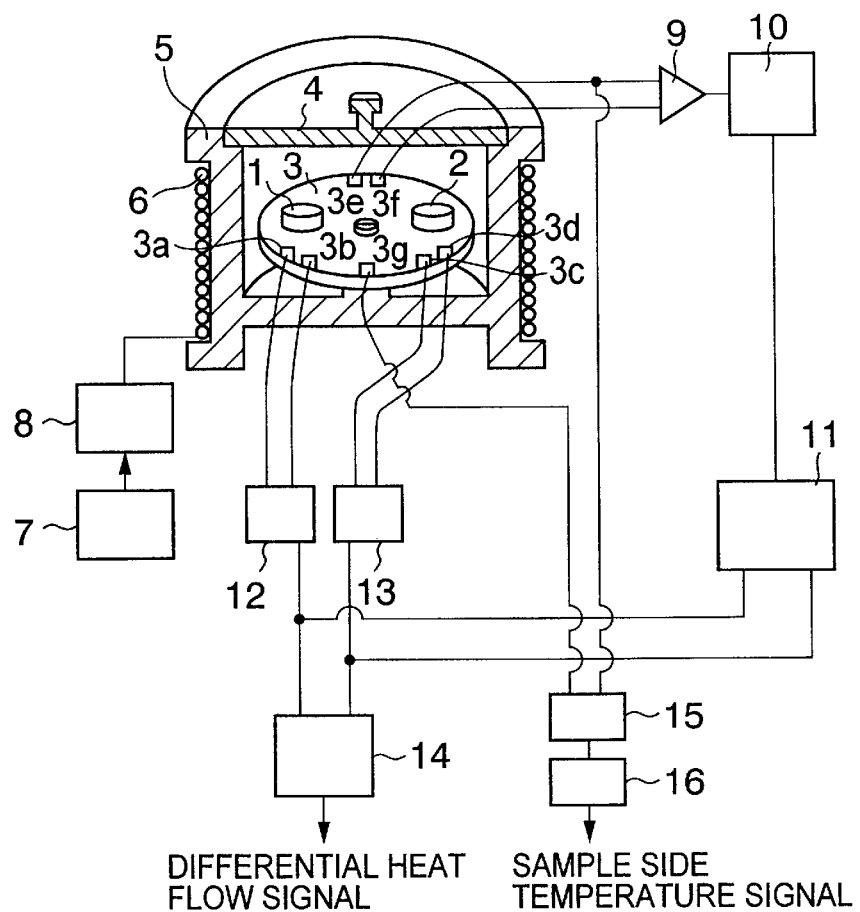
FIG. 1 is a block diagram showing an embodiment of the present invention, also including a partial cross section.

FIG. 1 shows the configuration of a differential scanning calorimeter of the present invention. Reference numeral 1 is a sample holder into which a sample is placed, and reference numeral 2 is a reference holder into which a thermally stable reference is placed. The sample holder 1 and the reference holder 2 are mounted on an insulating substrate on which regions are created for mounting the sample and the reference. In the embodiment, the insulating substrate 3 is a disk-shaped alumina substrate, and circuit pattern junction points using gold and palladium, and resistive circuit patterns using platinum, are applied on regions for mounting the sample and the reference. A central part of the insulating substrate 3 is screwed onto a central section of a cylindrical silver heat sink 5 having a substantially H-shaped cross section, using inconel type screws. A silver heat sink cover 4 is provided on an upper part of the heat sink 5, and the sample holder 1, reference holder 2 and insulating substrate 3 are contained by the heat sink 5 and the heat sink cover 4. A furnace control heater 6 coated with insulation is wound a side surface of the heat sink 5.

A furnace control circuit 8 is connected to a program function generator 7 for generating a program temperature signal for thermal analysis, and the furnace control circuit 8 appropriately adjusts output of the furnace control heater 6 that is connected to the furnace control circuit 8 to perform control so that the temperature of the heat sink 5 is varied in response to a program temperature function.

Figure 2:
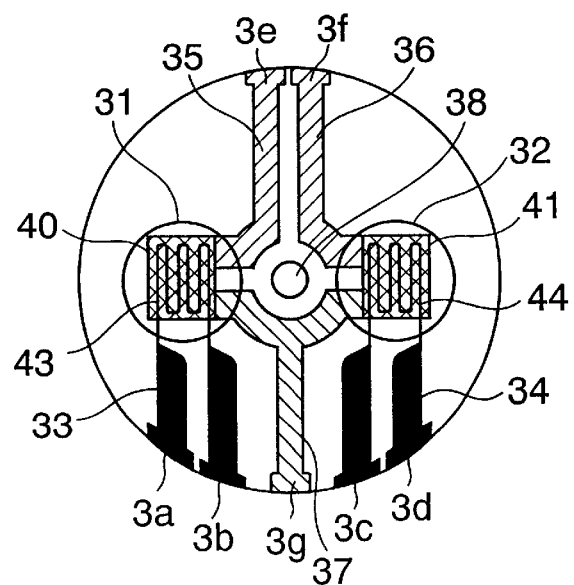
FIG. 2 is a detailed drawing of a circuit pattern of an insulating substrate used in the embodiment.

The circuit pattern of the insulating substrate 3 is shown in detail in FIG. 2. Reference numeral 3 is the alumina insulating substrate, and a central through hole 38 is provided so that the insulating substrate 3 can be screwed to a central part of the heat sink 5. Circular regions 31 and 32 respectively represent regions for mounting the sample and the reference, and the sample holder 1 and the reference holder 2 are mounted inside these regions. Reference numeral 33 is a platinum pattern applied inside the sample side region 31 on the insulating substrate 3, and the inside of the region 31 acts as a sample side compensation heater 43, and also has a function as a lead line at thick circuit patterns at places where it is outside the region 31. At an end section of the insulating substrate, there are terminals 3a and 3b for lead line connection to the outside. Reference numeral 34 is a platinum pattern similarly applied inside the reference side region 32 on the insulating substrate 3, and inside the region 32 acts as a reference side compensation heater 44, and also has a function as a lead line at thick surface patterns at places where it is outside the region 32. At an end section of the insulating substrate, there are terminals 3c and 3d for lead line connection to the outside. As will be clear from the drawing, the platinum patterns 33 and 34 are arranged symmetrically on the sample side and reference side. In the differential scanning calorimeter, symmetry of the sample side and the reference side is one important factor in improving noise reduction and stability.

The platinum patterns 33 and 34 are coated with a thin insulating film using alumina or alumina nitride at parts of the regions 31 and 32, namely at the parts of the sample side compensation heater 43 and the reference side compensation heater 44, in order to electrically insulate from the upper surface. Reference numerals 35 and 36 are gold circuit patterns applied on the insulating substrate 3, and are applied in quadrilateral shapes on the thin insulating film coated on the upper surfaces of the sample side compensation heater 43 and the reference side compensation heater 44 at inner sides of the regions 31 and 32. Reference numeral 37 is a palladium circuit pattern applied on the insulating substrate 3, and is applied in a shape joining above the quadrilateral shape regions of the gold circuit patterns 35 and 36 at inner sides of the regions 31 and 32. Then, the upper surface of the palladium circuit pattern 37, at parts of the regions 31 and 32, is coated with a thin insulating film using another layer of alumina or alumina nitride in order to get electrical insulation. Similarly to the platinum patterns 33 and 34, gold circuit patterns 35 and 36 and palladium circuit patterns 37 are arranged symmetrically on the sample side and reference side.

Figures 3A, 3B, 3C:
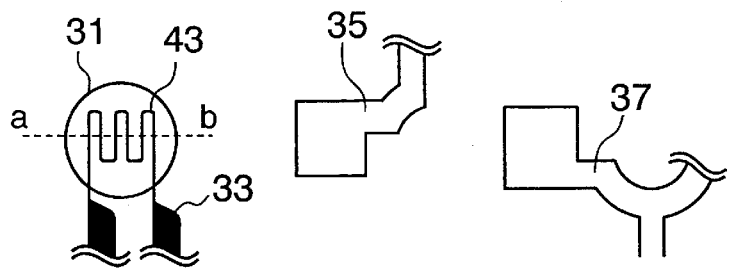
FIGS. 3A–3C are drawings showing a sequence of forming circuit patterns.
Figure 4:
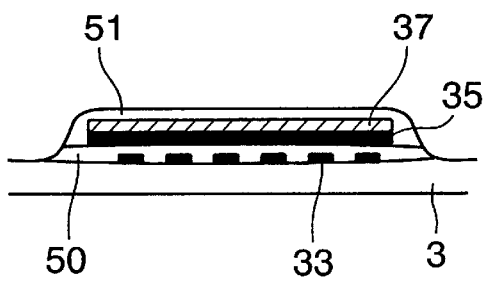
FIG. 4 is a cross sectional drawing along line a–b in FIG. 3.

FIGS. 3A–3C shows an order of forming these circuit patterns, and particularly an enlargement of the vicinity of the sample side region 31. First of all, the circuit pattern 33 using platinum is applied on the insulating substrate 3. Next, the thin alumina insulating film is applied on part of the region 31. The gold circuit pattern 35 is then applied on the thin alumina insulating film. Following that, at the region 31 the palladium circuit pattern 37 is superimposed on the gold circuit pattern 35 and applied in the shape of joints. Finally, a thin alumina insulating film is applied on part of the region 31. FIG. 4 is a cross sectional drawing along line a–b in FIG. 3, and shows the structure of the lowermost alumina insulating substrate 3, the platinum pattern 33 on top of that, then the alumina insulating film 50, the gold pattern 35, the palladium pattern 37 joining with the gold pattern 35, and the uppermost thin alumina insulating film 51.

The gold patterns 35 and 36 are formed into terminals 3e and 3f for lead line connection to the outside at end parts of the insulating substrate, and the palladium pattern 37 is formed into a terminal 3g for lead line connection to the outside at an end part of the insulating substrate. A circuit between the terminals 3e and 3f forms a gold-palladium-gold differential connection, and at regions 31 and 32 flat surface joining are performed using two types of metal at the quadrilateral sections shown in FIG. 2. Accordingly, at respective join surfaces an electromotive force corresponding to average temperature at that region is generated due to Seebeck effect, and if a voltage is measured at the terminals 3e and 3f the difference in electromotive force corresponding to a temperature differential between the regions 31 and 32 is measured. Also, if the voltage of the terminals 3e and 3f is taken out and compensated by an appropriate cold junction circuit, it is possible to measure the temperature of the region 31. Similarly, if the voltage of the terminals 3f and 3g is taken out and compensated by an appropriate cold junction circuit, it is possible to measure the temperature of the region 32. That is, the junction surfaces at the regions 31 and 32 function respectively as a sample side temperature sensor 40 and a reference side temperature sensor 41.

In this example, a description has been given of a method where a platinum circuit pattern as a compensation heater is first made on the alumina substrate, and then a gold and palladium circuit pattern is formed on the platinum circuit pattern as a temperature sensor, but it is also possible to first make the gold and palladium circuit pattern on the alumina substrate and then make the platinum circuit pattern as a compensation heater on the gold and palladium circuit pattern after coating with an insulating film.

Taking out of the lead lines from each of the terminals is carried out as follows. At the terminals 3e and 3f, gold wires are connected as lead lines by means of welding, crimping, high temperature brazing of BAg8, etc, or by providing through holes in the terminals and mechanically fixing using silver screws and nuts that are heat resistant. Also, at the terminal 3g, a palladium wire is connected as a lead line by similar means to that for the terminals 3e and 3f. At the terminals 3a, 3b and 3c, silver wires are connected as lead lines by means of high temperature brazing, such as BAG8, etc, or by providing through holes in the terminals and mechanically fixing using silver screws and nuts that are heat resistant.

Circular sections of the regions 31 and 32 can actually be drawn by an appropriate method, but it is also possible, for example, to have a distinctive shape at a boundary etc, of the thin alumina insulation film applied on the upper surface of the palladium pattern and the insulating substrate 3. It is preferable for the regions for mounting the sample holder 1 and the reference holder 2 to be appropriately distinguishable.

Returning again to FIG. 1, the terminals 3e and 3f for differential temperature detection are connected via lead lines to an amplifier 9, and the output of the amplifier 9 is connected to a converter 10 for converting from electromotive force difference to a temperature difference. The converter 10 is connected to a differential thermal compensation arithmetic circuit 11, and the differential thermal compensation arithmetic circuit 11 is connected to a sample side heater current control circuit 12 and a reference side heater current control circuit 13. Each heater current control circuit 12 and 13 is connected to a sample side compensation heater 43 through sample side compensation heater terminals 3a and 3b, and to a reference side compensation heater 44 through reference side compensation heater terminals 3c and 3d. Also, a computing unit 14 is connected to the sample side heater current control circuit 12 and the reference side heater current control circuit 13. The terminals 3e and 3g are connected through lead lines to a cold junction compensation circuit 15. Output from the cold junction compensation circuit 15 is connected to a thermoelectromotive force to a temperature converter 16, and a sample side temperature signal is output.

The differential thermal compensation arithmetic unit supplies a command to the sample side heater current control circuit 12 and the reference side heater current control circuit 13, based on output from the electromotive force/temperature difference converter 10, so that this output becomes zero. Output from each heater current control circuit 12 and 13 is sent to the sample side compensation heater 43 and to the reference side compensation heater 44 and the current flowing in the respective heaters is controlled. With this embodiment, an appropriate constant current is respectively supplied to the sample side compensation heater 43 and the reference side compensation heater 44 from the sample side heater current control circuit 12 and the reference side heater current control circuit 13, and after the differential thermal compensation arithmetic circuit 11 has carried out proportional arithmetic and appropriate amplification based on output from the electromotive force/temperature difference converter 10, control is performed to amplify the output from the sample side heater current control circuit 12 in the event that the sample side temperature is lower than the reference side temperature, and conversely, to reduce the output from the sample side heater current control circuit 12 in the event that the sample side temperature is higher than the reference side temperature. Based on output of each of the heater current control circuits 12 and 13, a difference in power consumed per consumption time respectively by the sample side compensation heater 43 and the reference side compensation heater 44 is calculated by the computation unit 14, and output as a differential heat flow signal.

Next, the operation of the device shown in FIG. 1 will be described.

First, a operator open the heat sink cover 4, then places the sample container 1 containing the sample to be measured and the reference material container 2 containing the reference material, for which the thermal stability is verified in the temperature range for which measurements will be taken, at specified places on the insulating substrate, and closes the heat sink cover 4.

Next, in accordance with a commence measurement command from the operator; a program temperature signal that has been input by the operator is output from the program temperature function generator 7. A program temperature signal output from the program temperature function generator 7 is sent to the furnace control circuit 8, and the temperature of the heat sink 5 is controlled so as to become the program temperature by operation of the furnace control circuit 8. Since the heat sink 5 is made from silver having good thermal conductivity, if a temperature gradient arises inside the heat sink 5, heat transfer occurs immediately and there is a function of canceling temperature distribution. Heat from the heat sink is transferred to the insulating substrate 3 fixed to the central part of the heat sink 5, heat is respectively conveyed to the sample inside the sample holder 1 and to the reference material inside the reference holder 2 through the insulating substrate 3, and as a result, the sample and the reference material are respectively controlled so as to approach the program temperature. In actual fact, a temperature rise of the sample and the reference mounted on the insulating substrate 3 is delayed compared to the center of the heat sink, due to the thermal resistance inside the insulating substrate 3. Accordingly, if the heat sink rises steadily in temperature according to the program temperature, the sample and the reference mounted on the insulating substrate 3 also rise in temperature steadily but with a delay.

On the other hand, simultaneously with a commence measurement command from the operator, control commences in order to return a temperature difference between the sample side and the reference side to zero by the action of the differential thermal compensation arithmetic circuit 11, sample side heater current control circuit 12 and reference side heater current control circuit 13. As a result of this, the reference side temperature rises steadily in line with the program temperature with a form of the heat flux arising due to fixed current supplied to the reference side compensation heater 44 from the reference side heater current control circuit 13 added to the steady heat flux from the heat sink. On the other hand, for the sample side temperature also, in the event that there is no thermal variation such as transfer to the sample, in addition to the steady heat flow from the heat sink 5, current is supplied from the sample side heater current control circuit 12 to the sample side compensation heater 43 so as to coincide with the temperature rise of the reference side (namely so that a temperature difference between the sample side and the reference side returns to zero), and as a result there is a steady rise in accordance with the program temperature, similarly to the reference side. Accordingly, the chain structure made up of the sample side temperature sensor 40, the reference side temperature sensor 41, the amplifier 9, the converter 10, the differential thermal compensation arithmetic unit 11, the sample side heater current control circuit 12, the reference side heater current control circuit 13, the sample side compensation heater 43 and the reference side compensation heater 44 constitutes a negative feedback loop, the function of bringing the temperature of the sample holder 1 and the reference holder 2 together is continued to thus always keep the temperature of them both substantially the same.

In a measuring process for raising the sample temperature at a constant rate, if transition of sample with heat change, the temperature of the sample will temporarily rise or fall and a temperature difference will arise between the sample holder 1 and the reference holder 2, but this difference is immediately returned to zero by the negative feedback loop. It is therefore possible to ascertain how much excess heat is absorbed or emitted by the sample compared to the reference material by obtaining a difference in power consumed (a square of resistance value multiplied by electrical current value) by the sample side compensation heater 43 and the reference side compensation heater 44. This difference in electrical power is calculated by the computation unit 14 and output as a differential heat flow signal, serves in analysis of the sample, and a function as a differential scanning calorimeter is realized.

In the chain of operations of this device, a significant point is the structure of temperature difference detectors constituting a trigger for the negative feedback control to the compensation heaters. In the differential scanning calorimeter having the structure of the embodiment, in obtaining an appropriate performance the temperature difference detectors must have a stability of at least $\frac{1}{10000}$th of a degree. With temperature difference detectors of the related art constructed using platinum resistors, precise measurement of those resistors is necessary for temperature detection, and generally a bridge circuit is built, an applied voltage for resistance value detection is applied, current flows in the resistors, and resistance value is detected from a potential difference occurring in the bridge circuit. However, this method has a problem that it is theoretically impossible to avoid self generation of heat in the resistors themselves, which causes variation in the temperature by the mere act of detecting temperature. In the case where temperature difference detection having a stability of at least $\frac{1}{10000}$th of a degree is required, if there is temperature variation caused by self heat generation at the time of temperature detection with an initial trigger, this variation is amplified because of negative feedback of the compensation heater based on this temperature variation, and as a result there was a problem that it was difficult to obtain stable temperature control.

However, with temperature measurement utilizing electromotive force due to the Seebeck effect shown in the embodiment, temperature measurement is theoretically passive and there is no temperature variation in the detector itself accompanying temperature detection. Accordingly, even when detecting temperature difference with the structure shown in the embodiment and performing negative feedback with the compensation heater, there is no temperature fluctuation originating in the temperature detection system which means that as a result temperature control having a stability of at least $\frac{1}{10000}$ of a degree becomes possible.

Figure 5:
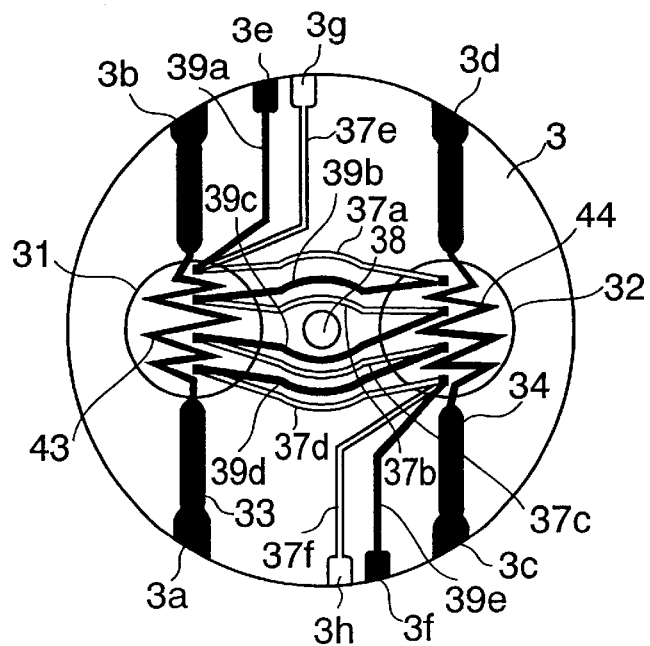
FIG. 5 is a detailed drawing showing an insulating substrate 3 (second example) using another circuit pattern.

FIG. 5 is a detailed drawing showing an insulating substrate 3 using another circuit pattern (second example). With this example, the circuit pattern for temperature difference detection and the circuit pattern for compensation heaters are formed on the same surface of the insulating substrate. An alumina insulating substrate 3, central through hole 38, and circular regions 31 and 32 for mounting the sample and the reference are respectively the same as in the example of FIG. 2. A sample side platinum pattern 33, applied inside the sample side region 31 on the insulating substrate 3, acts as a sample side compensation heater 43 inside the region 31, and also has a function as a lead line at thick surface patterns at places where it is outside the region 31. Terminals 3a and 3b for lead line connection to the outside are formed at end sections of the insulating substrate. Reference numeral 34 is a platinum pattern similarly applied inside the reference side region 32 on the insulating substrate 3, and the inside of the region 32 acts as a reference side compensation heater 44, and also has a function as a lead line at thick circuit patterns at places where it is outside the region 32. At an end section of the insulating substrate, there are terminals 3c and 3d for lead line connection to the outside.

Circuit pattern 39a–39e shown by black lines in the drawings are gold circuit patterns applied on the insulating substrate 3, while circuit patterns 37a–37f shown by white lines are palladium circuit patterns similarly formed on the insulating substrate 3. 39a and 39e constitute respective terminals 3e and 3f at end sections of the insulating substrate. The circuit patterns are connected from terminal 3e to terminal 3f through 39a, 37a, 39b, 37b, 39c, 37c, 39d, 37c, and 39e. A total of four points, namely a point of connection between 39a and 37a, a point of connection between 39b and 37b, a point of connection between 39c and 37c, and a point of connection between 39d and 37d, are respectively formed inside the sample side region 31, while a total of four points, namely a point of connection between 37a and 39b, a point of connection between 37b and 39c, a point of connection between 37c and 39d, and a point of connection between 37d and 39e, are respectively formed inside the reference side region 32.

Gold and palladium connections alternate between the terminal 3e and the terminal 3f, and respective connection points have a differential layout with four each on the sample side and the reference side. That is, between the terminal 3e and the terminal 3f, an electromotive force difference arises at the 4 pairs of gold-palladium thermocouples corresponding to temperature difference between the sample side and the reference side. The four pairs of connection points at the sample side and the reference side respectively constitute sample side and reference side temperature sensors 40 and 41. 37e and 37f are palladium circuit patterns, one end of each being respectively connected to a connection point of the gold pattern 39a and the palladium pattern 37a, and a connection point of the gold pattern 39e and the palladium pattern 37d, the other end of each constituting respective terminals 3g and 3h of the end sections of the insulating substrate 3. The terminals 3e and 3g can perform sample side temperature measurement, while the terminals 3f and 3h can perform reference side temperature measurement. With this example also, the circuit patterns for temperature measurement and the circuit patterns for the compensation heaters are arranged symmetrically on the sample side and reference side. The palladium pattern 37h does not have to be specially provided and can be incorporated into a differential scanning calorimeter having the structure shown in FIG. 1, but it is provided with the object of maintaining symmetry of the pattern.

Figure 6:
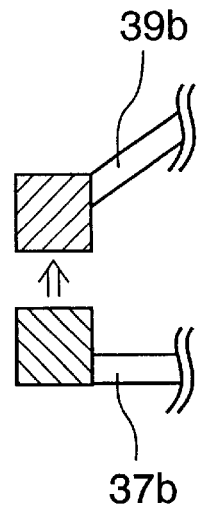
FIG. 6 is a drawing showing a formation method in the vicinity of a junction region of a gold circuit pattern and a palladium circuit pattern.

Construction of the circuit patterns and construction of the connection points is as described below, for example. First of all, after performing appropriate masking on the alumina substrate (insulating substrate 3), the platinum circuit pattern is formed by means such as vapor deposition or sputtering. Then, after performing similar appropriate masking, the gold circuit pattern is formed by means such as vapor deposition or sputtering, and after again performing appropriate masking, the palladium circuit pattern is formed by means such as vapor deposition or sputtering. FIG. 6 is a drawing showing a formation method in the vicinity of the junction region of the gold circuit pattern 39b and the palladium circuit pattern 37b. The gold circuit pattern 39b is assumed in advance so as to form a connection point of the quadrilateral region shown by diagonal lines in FIG. 6, and makes a gold circuit pattern. Next, the palladium circuit pattern 37b is made by superimposing a quadrilateral region shown similarly by diagonal lines in FIG. 6 over a connection point assumed region of the already formed gold pattern. The resulting superimposed quadrilateral regions constitute connection points, and outside that constitute gold and palladium circuit patterns as lead lines. The shape of these connection regions need not be quadrilateral and can be other shapes, and the necessary function will be achieved as long as they are superimposed. Finally, a thin coating of insulation is applied on the circuit patterns of the regions 31 and 32 using a material having heat resistance, such as alumina or glass. The coating can be applied to the entire surface except for the terminal parts.

Similar affects are also obtained if the insulating substrate 3 to which the circuit patterns of FIG. 5 are applied is incorporated into the differential scanning calorimeter shown in FIG. 1. It is possible to carry out exactly the same operations as described in the embodiment of FIG. 1 by connecting the terminals 3e and 3f to the amplifier 9, connecting the terminals 3e and 3g to the cold junction circuit 15, and connecting the terminals 3a, 3b and 3c, 3d respectively to the sample side heater current control circuit 12 and the reference side heater current control circuit 13.

Figure 7:
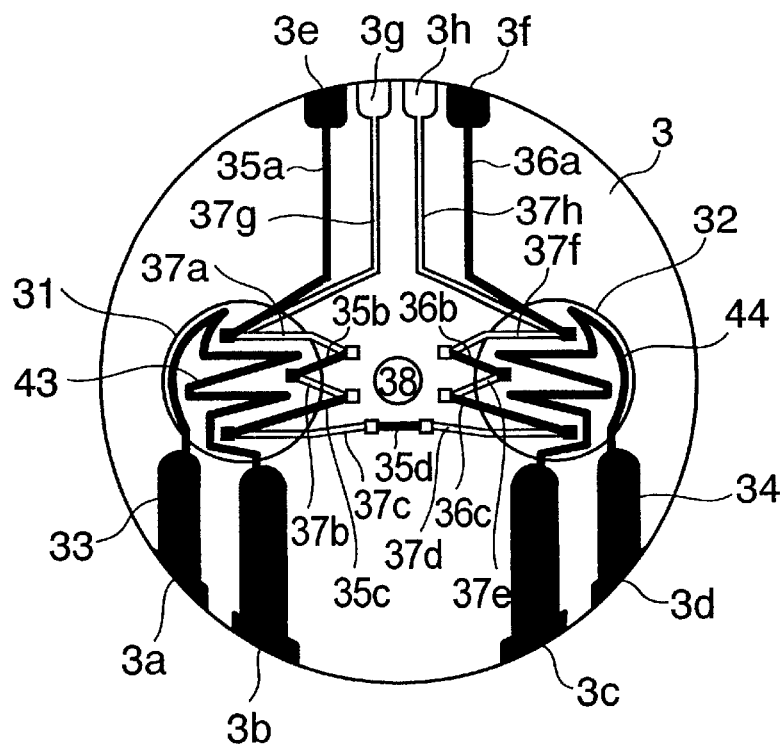
FIG. 7 is a detailed drawing showing an insulating substrate 3 (third example) using another circuit pattern.

FIG. 7 is a detailed drawing showing an insulating substrate 3 using another circuit pattern (third example). In this example also, the circuit pattern for temperature difference detection and the circuit pattern for compensation heaters are formed on the same surface of the insulating substrate, and symmetrically on the sample side and the reference side. An alumina insulating substrate 3, central through hole 38, and circular regions 31 and 32 for mounting the sample and the reference are respectively the same as in the example of FIG. 2. A sample side platinum pattern 33, applied inside the sample side region 31 on the insulating substrate 3, acts as a sample side compensation heater 43 inside the region 31, and also has a function as a lead line at thick circuit patterns at places where it is outside the region 31. Terminals 3a and 3b for lead line connection to the outside are formed at end sections of the insulating substrate. Reference numeral 34 is a platinum pattern similarly applied inside the reference side region 32 on the insulating substrate 3, and inside the region 32 acts as a reference side compensation heater 44, and also has a function as a lead line at thick circuit patterns at places where it is outside the region 32. Terminals 3c and 3d for lead line connection to the outside are formed at end sections of the insulating substrate. Reference numerals 35a–35d and 36a–36c are gold circuit patterns applied on the insulating substrate, while reference numerals 37a–37h are palladium circuit patterns applied on the insulating substrate 3. As shown in FIG. 7, circuit pattern connections are made up by 35a, 37a, 35b, 37b, 35c, 37c, 35d, 37d, 36c, 37e, 36b, 37f and 36a, and 35a and 36a constitute respective terminals 3e and 3f at end sections of the insulating substrate.

Also, connection points between 35a and 37a, 35b and 37b, and 35c and 37c are formed in the sample side region 31, while connection points between 37a and 35b, 37b and 35c, and 37c and 35d are formed in the vicinity of the through hole 38 close to the center of the insulating substrate 3. Similarly connection points between 36a and 37f, 36b and 37e, and 36c and 37d are formed in the reference side region 32, while connection points between 37f and 36b, 37e and 36c, and 37d and 35d are formed in the vicinity of the through hole 38 close to the center of the insulating substrate 3.

As will be clear from FIG. 7, connections from 35a to 35d constitute a differential arrangement, with connection points arranged in three pairs between the sample side region 31 and the vicinity of the through hole 38 of the insulating substrate 3, and is an arrangement that enables output of a temperature differential between the sample side region 31 and the vicinity of the through hole 38. Similarly, connections from 36a to 35d also constitute a differential arrangement, with connection points arranged in three pairs between the reference side region 32 and the vicinity of the through hole 38, and is an arrangement that enables output of a temperature differential between the reference side region 32 and the vicinity of the through hole 38. The vicinity of the through hole 38 is an inlet for heat flux from the heat sink 5, and stably becomes a temperature almost equal to that of the heat sink 5. Accordingly, outputs of the connections from 35a through 35d to 36a resultantly constitute an output of a temperature difference between the sample side region 31 and the reference side region 32. Connection points arranged inside the sample side region 31 and connection points arranged inside the reference side region 32 then respectively constitute sample side and reference side temperature sensors 40 and 41. 37g and 37h are palladium circuit patterns, one end of each being respectively connected to a connection point of the gold pattern 39a and the palladium pattern 37a, and a connection point of the gold pattern 36a and the palladium pattern 37f, the other end of each constituting respective terminals 3g and 3h of the end sections of the insulating substrate 3. The terminals 3e and 3g can perform sample side temperature measurement, while the terminals 3f and 3h can perform reference side temperature measurement. Formation of the circuit patterns and connection points, and insulation coating of the surface, is carried out in the same way as the example shown in FIG. 5.

Similar effects are also obtained if the insulating substrate 3 to which the circuit patterns of FIG. 7 are applied is incorporated into the differential scanning calorimeter shown in FIG. 1. It is possible to carry out exactly the same operations as described in the embodiment of FIG. 1 by connecting the terminals 3e and 3f to the amplifier 9, connecting the terminals 3e and 3g to the cold junction circuit 15, and connecting the terminals 3a, 3b and 3c, 3d respectively to the sample side heater current control circuit 12 and the reference side heater current control circuit 13.

Also, with this embodiment, the connections points for temperature measurement are made of two types of metal, gold and palladium, but the same effects are obtained even if a circuit patterns are formed from metal and metal alloy or two types of alloy, for example, platinum and platinum rhodium alloy, chromel and alumel, or chromel and constantan. As a construction method for the circuit patterns in the case of an alloy, sputtering is mainly used. Also, the insulating substrate has been described as an alumina substrate in this embodiment, but the same effects will be obtained as long as it has heat resistance and the surface is a material having electrical insulation properties (for example, a ceramics such as silicon nitride or alumina nitride, glass, or forming an alumina layer uniformly over the surface of a aluminum substrate by a oxidization process).

In a differential calorimeter having temperature sensor and compensation heater circuit patterns formed on an insulating substrate, and this insulating substrate being fixed inside a heat sink made of good heat conductive a material, temperature difference measuring side circuit patterns are constructed using two kinds of metal or alloy, and by finding out an electromotive force difference there is no occurrence of self heat generation of resistors themselves as in temperature difference measurement with metallic resistors of the related art, and as a result it is possible to have stable temperature control without having any affect on negative feedback control of a compensation heater for triggering this temperature difference. In particular, there is the effect of enabling temperature difference control having a stability of better than $\frac{1}{10000}$th of a degree. Also, with the differential scanning calorimeter having the structure described in the above embodiments, a temperature difference between a heat sink surrounding a sample and a reference, and the sample and the reference, is small, which means that the sample and the reference are thermally insulated from the outside of the heat sink and heat exchange of a direct connection to the outside is controlled, it is made difficult for drift to occur in a differential heat flow signal, it means that disadvantage of a power compensation type DSC are dismiss.

Moreover, it is possible to control electrical power supplied to heaters individually in the vicinity of the sample and the reference so that the temperature difference is immediately returned to zero, and further, since a proportional coefficient that is a control parameter in this control can be optimally adjusted, so a differential heat flow signal having good responsiveness is obtained and results can be obtained that collectively dismiss a disadvantage of a heat flux type differential scanning calorimeter.

What is claimed is:

1. A differential scanning calorimeter comprising: a heat sink made of a superior heat conductive material having a space for setting a sample and reference material inside; an insulating substrate fixed inside the heat sink and provided with a first region for mounting the sample and a second region for mounting the reference; a first circuit pattern having junctions of two kinds of alloy or metal at each of the first and second regions; a differential thermal detection circuit for detecting a temperature difference between the sample and the reference mounted on the insulating substrate by detecting a difference in thermoelectromotive force between the junctions of the first region and those of the second region; second circuit patterns made of metallic resistors provided at each of the first and second regions; a differential heat compensation circuit for allowing appropriate current to flow in each of the second circuit patterns so as to continually return output of the differential thermal detection circuit to zero; a temperature program generator for outputting a target temperature value periodically; and a heat sink temperature controller for controlling the temperature of the heat sink in response to output of the temperature program generator, whereby the first circuit pattern enables the detection of the temperature difference without self heat generation which temperature difference is inputted to the differential heat compensation circuit.

2. The differential scanning calorimeter of claim 1, wherein the first circuit pattern applied so as to form junction of two kinds of metal or alloy, and the second circuit patterns formed by means of the metallic resistors, are applied so that they are not crossing to each other on the same plane on the insulating substrate.

3. The differential scanning calorimeter of claim 1, wherein a thin insulating layer is applied on the first circuit pattern applied so as to form junction of two kinds of metal or alloy, and the second circuit patterns formed by means of the metallic resistors are applied on that thin insulating layer.

4. The differential scanning calorimeter of claim 1, wherein a thin insulating layer is applied on the second circuit patterns formed by means of the metallic resistors, and the first circuit pattern applied so as to form junction of two kinds of metal or alloy is applied on that thin insulating layer.

* * * * *